US010835391B2

(12) United States Patent
Goldfarb et al.

(10) Patent No.: US 10,835,391 B2
(45) Date of Patent: *Nov. 17, 2020

(54) JOINTED MECHANICAL DEVICES

(71) Applicant: VANDERBILT UNIVERSITY, Nashville, TN (US)

(72) Inventors: Michael Goldfarb, Franklin, TN (US); Skyler Dalley, Shaker Heights, OH (US); Huseyin Atakan Varol, Astana (KZ); Tuomas Wiste, Genoa (IT)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/209,474

(22) Filed: Dec. 4, 2018

(65) Prior Publication Data

US 2019/0125550 A1    May 2, 2019

Related U.S. Application Data

(60) Continuation of application No. 15/049,826, filed on Feb. 22, 2016, now Pat. No. 10,172,725, which is a
(Continued)

(51) Int. Cl.
*A61F 2/54* (2006.01)
*A61F 2/58* (2006.01)
(Continued)

(52) U.S. Cl.
CPC .............. *A61F 2/586* (2013.01); *A61F 2/583* (2013.01); *A61F 2/72* (2013.01);
(Continued)

(58) Field of Classification Search
CPC .... A61F 2/58; A61F 2/586; A61F 2/54; A61F 2/68; A61F 2002/6827; A61F 2002/704
See application file for complete search history.

(56) References Cited

U.S. PATENT DOCUMENTS 5,383,939 A    1/1995  James
5,650,704 A    7/1997  Pratt
(Continued)

FOREIGN PATENT DOCUMENTS

EP    1195151    4/2002
EP    1043003    5/2004
(Continued)

OTHER PUBLICATIONS

International Search Report and Written Opinion for International Patent Application No. PCT/US2010/046050, dated Feb. 24, 2011 (11 pages).
(Continued)

*Primary Examiner* — Bruce E Snow
(74) *Attorney, Agent, or Firm* — Nixon Peabody LLP

(57) ABSTRACT

A jointed mechanical device is provided. The device includes at least one element having a fixed end and a deflectable end. The device also includes at least one actuating structure having a first end coupled to at least the deflectable end of the element, where the actuating structure includes at least one elastic element in series with at least one non-elastic element. The device further includes at least one force actuator configured to apply an actuator force to a second end of the actuating structure. Additionally, the device includes a control system for adjusting an operation of the force actuator based at least one actuation input, an amount of the actuator force, and an amount of displacement generated by the force actuator.

8 Claims, 6 Drawing Sheets

Related U.S. Application Data division of application No. 13/391,553, filed as application No. PCT/US2010/046050 on Aug. 20, 2010, now Pat. No. 9,265,625.

(60) Provisional application No. 61/235,421, filed on Aug. 20, 2009.

(51) Int. Cl.
*A61F 2/72* (2006.01)
*A61F 2/70* (2006.01)
*A61F 2/76* (2006.01)

(52) U.S. Cl.
CPC ... *A61F 2002/587* (2013.01); *A61F 2002/701* (2013.01); *A61F 2002/704* (2013.01); *A61F 2002/7615* (2013.01); *Y10T 74/20317* (2015.01); *Y10T 74/20329* (2015.01)

(56) References Cited

U.S. PATENT DOCUMENTS

| | | | |
|---|---|---|---|
| 6,896,704 | B1 | 5/2005 | Higuchi |
| 8,512,415 | B2 | 8/2013 | Herr |
| 9,265,625 | B2 | 2/2016 | Goldfarb |
| 10,172,725 | B2 | 1/2019 | Goldfarb |
| 2004/0049290 | A1 | 3/2004 | Bedard |
| 2004/0181289 | A1 | 9/2004 | Bedard |
| 2007/0123997 | A1 | 5/2007 | Herr |
| 2007/0219668 | A1 | 9/2007 | Takahashi |
| 2008/0114272 | A1 | 5/2008 | Herr |

FOREIGN PATENT DOCUMENTS

| | | |
|---|---|---|
| EP | 1477277 | 9/2008 |
| WO | WO 2008/098072 A1 | 8/2008 |

OTHER PUBLICATIONS

International Search Report and Written Opinion for International Patent Application No. PCT/US2010/046054, dated Feb. 24, 2011 (11 pages).

Akazawa et al.; "Compliant Grasp in a Myoelectric Hand Prosthesis"; Controlling Flexion Angle and Compliance with Electromyogram Signals, Technological Developments in Japan, IEEE Engineering in Medicine and Biology Magazine, IEEE Serivice Center, Piscataway, NJ, US; vol. 24, No. 4, pp. 48-56; Jul. 1, 2005; XP011136048.

Balasubramanian et al.; "Biological Stiffness Control Strategies for the Anatomically Correct Testbed (ACT) Hand"; 2008 IEEE International Conference on Robotics and Automation; Pasadena, CA; XP031340237, May 19, 2008, pp. 737-742.

Lee et al.; "Stiffness Control of the Coupled Tendon-Driven Robot Hand"; Proceedings of the International Conference on Systems, Man and Cybernetics, XP010132342, Oct. 17, 1993, pp. 710-715.

Tsujiuchi et al.; "Grasp Control Using Compliance Control with Variable Stiffness Matrix"; Proceedings of the 2003 IEEE/RSJ Int'l Conference on Intelligent Robots and Systems; Las Vegas, Nevada, USA; vol. 4, pp. 3294-3299; XP010671283; Oct. 27, 2003.

Wiste et al.; "Design of a Multifunctional Anthropomorphic Prosthetic Hand with Extrinsic Actuation"; 2009 IEEE 11th International Conference on Rehabilitation Robotics; Kyoto International Conference Center, Japan; XP031516352; Jun. 23, 2009, pp. 675-681.

JOINTED MECHANICAL DEVICES

CROSS-REFERENCE TO RELATED APPLICATIONS

This application is a continuation of U.S. application Ser. No. 15/049,826, filed Feb. 22, 2016, which is a divisional of U.S. application Ser. No. 13/391,553, filed Feb. 21, 2012, now U.S. Pat. No. 9,265,625, issued Feb. 23, 2016, which is a National Stage Entry of International Application No.: PCT/US10/46050, issued on Aug. 20, 2010, which claims priority to and the benefit of Provisional Application No. 61/235,421, filed Aug. 20, 2009, the contents of which are all hereby incorporated herein by reference in their entireties.

FIELD OF THE INVENTION

The present invention relates to powered mechanical devices, and more specifically to jointed mechanical devices.

BACKGROUND

In general, the motion of jointed mechanical devices, such as robotic hand prosthetic devices, can be controlled with control signals and/or sensors monitoring the motors within the jointed mechanical device. However, fine motor control of such devices is typically difficult to achieve, as the amount of feedback sensory information available in natural limbs and appendages greatly exceeds the amount of feedback information typically available in conventional jointed mechanical devices. Although some jointed mechanical devices have been constructed to include additional feedback sensors, the additional costs, complexity, and weight associated with such feedback sensor systems are generally impractical.

Additionally, the number of signals available for controlling such devices is fairly limited, resulting in only a few types of inputs being available for a relatively large number of components. For example, in some types of robotic prosthetic devices, a measurement of the electric potential generated by the muscles in a residual limb, commonly referred to as an electromyogram (EMG) signal, is used to control the movements of the prosthesis. In such devices, EMG signals can be used to command the forward and/or reverse velocity of one or more electric motors configured to actuate the prosthesis. One common type of robotic prosthetic device using EMG signals is a myoelectric hand and/or arm prosthetic device.

Hand and/or myoelectric prosthetic devices typically operate based on EMG signals generated by the muscles of the residual forearm or upper arm. However, a residual limb typically only produces a few usable EMG signals. Consequently, even though such prosthetic devices can be designed to be anthropomorphic to provide a visually pleasing prosthesis, the limited number of EMG signals generally results in limited utility. In the case of conventional myoelectric hand prostheses, only a sophisticated claw is generally provided. That is, these prosthetic devices are generally designed to provide a "pinch-type" operation, permitting the user to grasp an object but little else. Although, the ability to grasp and hold objects can be a significant improvement in the lifestyle of a hand and/or arm amputee, the utility of such devices is limited. Although more sophisticated designs are available, the additional costs, complexity, and weight associated with such devices are generally impractical.

SUMMARY

Embodiments of the present invention concern jointed mechanical devices. In a first embodiment of the invention, a device is provided. The device includes at least one element having a fixed end and a deflectable end. The device also includes at least one actuating structure having a first end coupled to at least said deflectable end of said element, where said actuating structure comprising at least one elastic element in series with at least one non-elastic element. The device further includes at least one force actuator configured to apply an actuator force to a second end of said actuating structure. Additionally, the device includes a control system for adjusting an operation of said force actuator based at least one actuation input, an amount of said actuator force, and an amount of displacement generated by said force actuator.

In a second embodiment of the invention, a device is provided. The device includes a base and at least one digit pivotably coupled to said base, where said digit comprising a plurality of phalangeal portions connected by a plurality of flexible joint portions. The device further includes at least one actuating structure having a first end coupled to a distal end of said digit, where said actuating structure comprising at least one elastic element in series with at least one non-elastic element. The device additionally includes at least one force actuator configured to apply an actuator force to a second end of said actuating structure. The device also includes a control system for adjusting an operation of said force actuator based at least one actuation input, an amount of said actuator force, and an amount of displacement generated by said force actuator.

In a third embodiment of the invention, a method is provided for controlling a jointed mechanical device comprising at least one element having a fixed end and a deflectable end, at least one actuating structure having a first end coupled to at least said deflectable end of said element, and at least one force actuator configured to apply an actuator force to a second end of said actuating structure, where said actuating structure comprises at least one elastic element in series with at least one non-elastic element. The method includes the step of monitoring an amplitude of at least one signal associated with at least one actuation input. The method also includes the step of determining an amount of said actuator force applied by said force actuator to said second end of said actuating structure and an amount of displacement generated by said force actuator. The method further includes the step of adjusting an operation of said force actuator based at least one said monitored amplitude, said amount of said actuator force, and said amount of displacement.

In a fourth embodiment of the invention, a prosthetic device is provided. The prosthetic device includes at least one member and a hand device coupled to the member. The hand device comprising a base and at least one digit pivotably coupled to said base, where said digit comprising a plurality of phalangeal portions connected by a plurality of flexible joint portions. The hand device also includes at least one actuating structure having a first end coupled to a distal end of said digit, where said actuating structure comprising at least one elastic element in series with at least one non-elastic element. The hand device further includes at least one force actuator configured to apply an actuator force to a second end of said actuating structure. The hand device additionally includes a control system for adjusting an operation of said force actuator based at least one actuation input, an amount of said actuator force, and an amount of displacement generated by said force actuator.

DETAILED DESCRIPTION

Figure 1A:
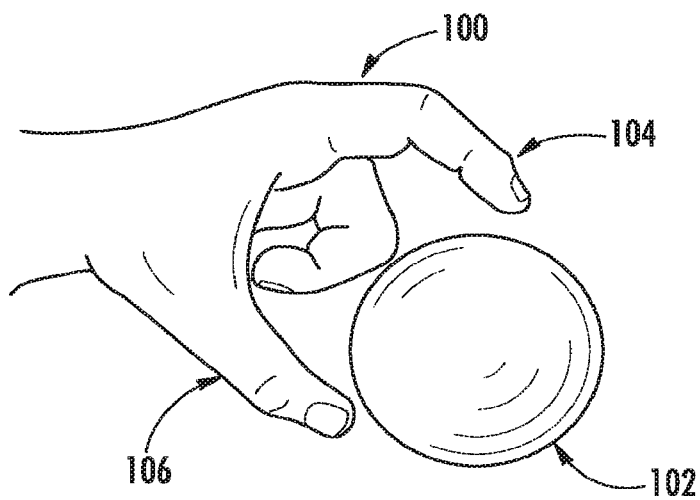
FIG. 1A-1C are diagrams showing grasping of a ball by a hand that is useful for understanding the various embodiments of the invention.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Although overall motion control of the hand or other appendage is important during gesturing, control of force is generally desirable during grasping. That is, a hand may apply different amount of forces before and after grasping or contacting an object. In general, a greater amount of force may be applied to move fingers quickly into place for grasping or contacting an object. Afterwards, the brain, based on feedback obtained from nerves in the arm and hand, automatically adjusts the amount force applied by the finger depending on the shape, size, and type of object. Such fine motor control is typically unachievable in jointed mechanical devices, as a large amount of sensory information is needed in conjunction with the ability to tune the amount of force being applied. The term "jointed mechanical device" as used herein, refers to any powered mechanical device having one or more movable joints, including, but not limited to, robotic prosthetic and robotic non-prosthetic devices. As described above, jointed mechanical devices can be configured to include a large number of sensors, but the additional costs, complexity, and weight associated with such feedback sensor systems are generally impractical. Additionally, the number of inputs available is typically limited. As a result, a user of such a device, such as a myoelectric prosthesis, can generally only provide an up/down signal for a particular direction or axis of motion. This configuration enables position control, but does not generally provide any type of force control.

To overcome the limitations of existing jointed mechanical devices, embodiments of the invention provide systems and methods for providing some amount of fine motor control in such devices designed for grasping or contacting an object. In particular, the various embodiments of the invention provide a jointed mechanical device that automatically switches between a motion control mode when the device is operating in free space and force control mode when the device grasps or contacts an object. This is conceptually illustrated in FIGS. 1A-1C.

FIG. 1A shows a diagram of a hand 100 about to grasp or contact an object, in this case a ball 102. In this pre-grasp or pre-contact stage, the digits of hand 100, such as index finger 104 and thumb 106 are positioned to approach ball 102. In general, this placement can occur very quickly and all motion in hand 100 is directed to the placement of these digits. Accordingly, in a robotic or prosthetic hand device, a motion control mode can be used during the pre-contact period to move the digits in such a device as quickly as possible to a contact point. However, the digit velocities during such a pre-contact period can result in an undesirable amount of force after contact.

Figure 1B:
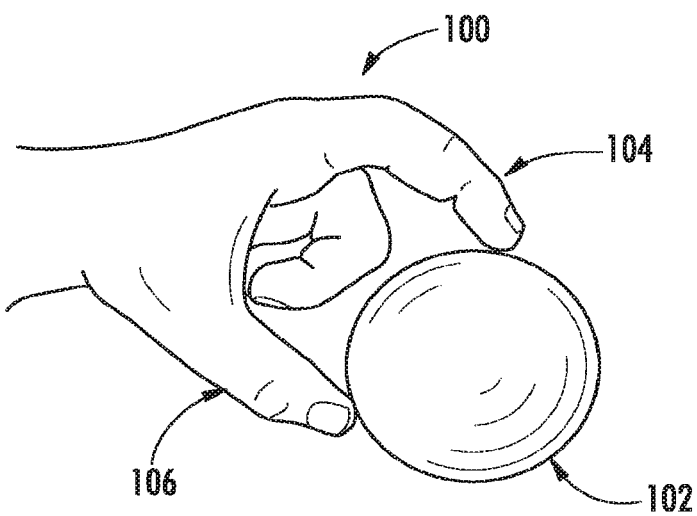
Figure 1C:
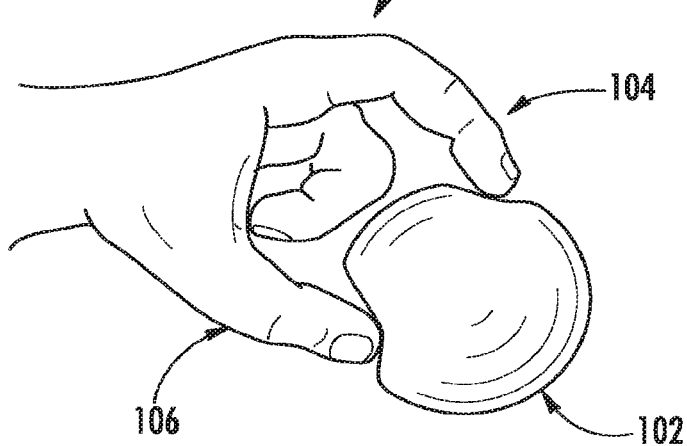

As illustrated in FIG. 1B, finger 104 and thumb 106 may come into contact with ball 102 at some point in time. As described above, the difficulty in most jointed mechanical devices is how to proceed from this point of contact without sophisticated sensory information. If the same force or rate of change in digit position used while approaching ball 102 is applied once contact has been made with ball 102, the resulting force may be too high, possibly damaging or distorting ball 102. Such distortion is shown in FIG. 1C, where the additional and continuing force crushes portions of ball 102.

In a natural hand, force is automatically adjusted by the brain based on sensory inputs. In a simplest sense, motion of the index finger 104 and thumb 106 is effectively halted or slowed to permit grasping of ball 102 without the need to crush ball 102. Therefore, the various embodiments of the invention provide a jointed mechanical device and associated control system, such that the point of contact with and object is detected, the operation of the device is subsequently changed to a force control mode such that events, such as crushing of the object, do not necessarily occur. For example, in a myoelectric prosthesis, the change in digit position (i.e., the force applied) in response to an EMG signal is altered. In particular, the force control mode can provide for a slower change in digit position as opposed to the change in digit position prior to contact during a motion control mode. Accordingly, the user is provided with a means of utilizing the typically limited number of myoelectric signals to control both gross and fine motor control. In particular, embodiments of the invention not only operate a jointed mechanical device in first mode prior to contact and a second mode subsequent to contact, but can detect the point of contact to trigger the change in mode.

In particular, the modes of operation in the various embodiments of the invention can be triggered without explicitly requiring force sensors or direct force control of the actuator. In particular, a structure and associated control system are provided that enable multiple modes from an otherwise dedicated motion controlled actuator. As a result, only limited sensing and electronic motion control is required for controlling operation of a jointed mechanical device, such as a robotic prosthetic device.

Although the various embodiments of the invention will be described with respect to a prosthetic hand device, this is for illustrative purposes only. One of ordinary skill in the art will recognize that the various embodiments of the invention can be applied to any type of jointed mechanical device configured for grasping, contacting, or holding objects. Furthermore, although only two modes of operation will be described below for the exemplary prosthetic hand device, the various embodiments of the invention are not limited in this regard. One of ordinary skill in the art will recognize that more than two modes of operation are possible, depending on the configuration of the device.

Figure 2:
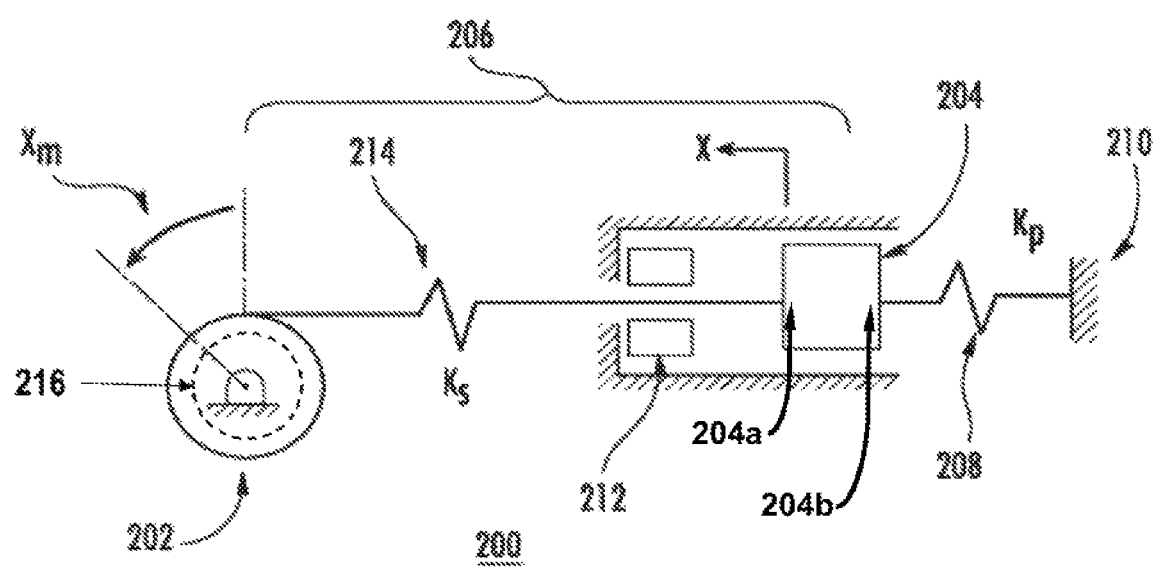
FIG. 2 shows a schematic diagram of an actuation system 200 for a prosthetic hand device in accordance with an embodiment of the invention.

FIG. 2 shows a schematic diagram of an actuation system 200 for a prosthetic hand device in accordance with an embodiment of the invention. As shown in FIG. 2, the system 200 includes a position-controlled force actuator 202 that causes motion of a digit or other deflectable or movable element 204 connected to actuator 202 by an actuating structure 206. In operation, as the position of the actuator 202 is changed, force is applied to actuating structure 206, resulting in the motion of element 204. In some embodiments, the system 200 can also include a parallel spring or restorative element 208 between a fixed end portion 204b of element 204 and a fixed point 210. The restorative element 208 is configured to counter the force applied to actuating structure 206 to effectively provide a parallel spring force defined by a stiffness (i.e., spring constant) $k_p$.

In some embodiments of the invention, the force actuator 202 can comprise an electric motor and pulley assembly configured to operate with a cable of the actuating structure 206. Additionally, such a configuration can also include a roller clutch 216 between a motor and a pulley in the force actuator 202. The roller clutch 216 can be used to lock a cable of the actuating structure in place, thus the element 204 is also locked at a position when the motor is turned off.

As described above, automatic switching between a motion control mode and a force control mode is provided in the various embodiments of the invention when an element comes into contact with an object. Referring back to FIG. 2, this switching should occur when element 204 comes into contact with rigid object 212. Such automatic control can be achieved by including in actuating structure 206 at least one elastic component 214 between element 204, at a deflectable end portion 204a, and actuator 202. The placement of the elastic component 214 between element 204 and actuator 202 effectively provides a spring force in series with components 202 and 204 defined by a stiffness $k_s$.

If the parallel (restorative) stiffness $k_p$ and the serial stiffness $k_s$ are known, a control methodology for switching between a motion control mode and a force control mode can be developed. For example, assuming the series stiffness and parallel stiffness are approximately the same order ($k_s \approx k_p$) and element 204 is not in contact with a rigid object 212, the amount of displacement x of the element 204 from a resting position will be in proportion to the amount of displacement provided by the force actuator, as shown below in Equation (1):

$$x = \frac{k_s}{k_s + k_p} x_m \quad (1)$$

where $x_m$ is the measured linear position at the force actuator. In embodiments of the invention using a motor applying a rotary force, $x_m$ can be derived from an angular measurement (i.e., a amount of rotation of the motor). Accordingly, when element 204 is not in contact with a rigid object, the relationship between actuator force and actuator displacement can be given by Equation (2):

$$F_m = \frac{k_p k_s}{k_s + k_p} x_m \quad (2)$$

Therefore, by monitoring actuator force and actuator displacement, it is possible ascertain when the element 204 has come into contact with rigid object 212. In embodiments of the invention utilizing electric motors, the actuator force and the actuator displacement can monitored by measuring, for example, an input current to the electric motor and an amount of rotation of the electric motor.

In particular, once the relationship in Equation (2) no longer holds true, this indicates that element 204 has come into contact with object 212. When this condition is detected, displacement provided by the actuator 202 needs to be controlled according to a force control mode. Once in contact with the object, the relationship between the amount of force provided by the force actuator and the amount of actuator displacement changes to:

$$F_g = k_s (x_m - x_{mo}) \quad (3)$$

where $x_{mo}$ is the amount of actuator displacement at the time of initial contact with an object. Therefore, by monitoring actuator force and actuator displacement, it is also possible ascertain when the element 204 is not contacting rigid object 212. That is, once the relationship in Equation (3) no longer holds true, this indicates that element 204 is no longer in contact with object 212.

Although the embodiment above has been described with respect to monitoring compliance with Equation (2) or Equation (3), the various embodiments of the invention are not limited in this regard. For example, in some embodiments of the invention, both Equation (2) and Equation (3) can be continually evaluated and a decision of whether of operate in a motion control mode or a force control mode can be made on the basis of which equation is being substantially met.

By using the control methodology described above, the motion of the prosthesis can be controlled in a motion control mode when gesturing, and in a force control mode when grasping or contacting an object. Furthermore, if a roller clutch is used to "lock in" a given motor position, the clutch will provide the dual function of locking the position of the prosthesis when gesturing or locking in the force being applied to an object when grasping.

Note that Equation (3) does not depend on the stiffness of the object. However, the detection of contact with the object, based on Equation (2), relies on the assumption that the object is stiff relative to $k_p$. If the object is compliant relative to $k_p$ (e.g., a sponge or other object having a stiffness $k_{object} < k_p$), the switch to a force control mode will be delayed. In general, force control is not as important in such cases, since either position or force control work equally well when grasping highly compliant objects.

In some embodiments of the invention, a robotic hand will likely have a covering comprising an elastomer and/or one or more other elastic materials to emulate the appearance of a natural hand. This covering will constitute a portion of the parallel stiffness in the robotic hand, and corresponding information regarding the covering can be provided to a controller to allow more accurate detection of contact with an object using Equation (2). In such embodiments, the stiffness of the covering and/or any other stiffnesses present in the robotic hand can be automatically mapped and/or detected in a calibration routine. During such a routine, the robotic hand can be commanded to slowly close and open while not grasping an object, while a controller monitors the motor position and current. The controller can then create a position/force map that represents the hand behavior in the absence of an object and use this map during normal operation of the robotic hand.

Figure 3:
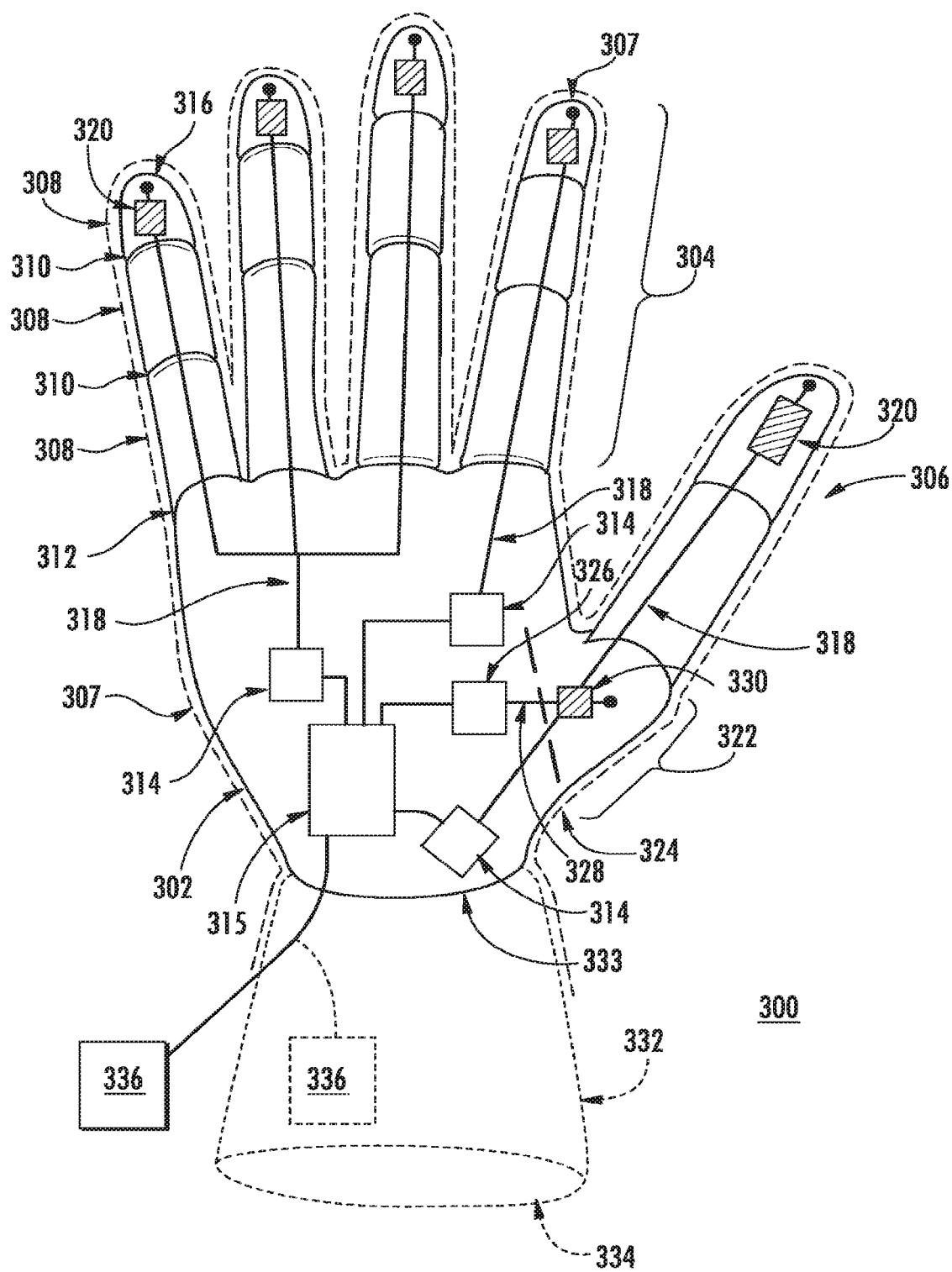
FIG. 3 is an anterior view of a prosthetic hand device 300 in accordance with an embodiment of the invention.

An exemplary prosthetic hand device for use with the methodology described above in shown in FIGS. 3-5. FIG. 3 is an anterior view of a prosthetic hand device 300 in accordance with an embodiment of the invention. As shown in FIG. 3, the device 300 includes a base 302 and digits comprising fingers 304, a thumb 306, or any other type of flexible or deflectable element. Optionally, the device can include a covering 307, as described above, and that can be composed of one or more elastic portions. Each of the digits in prosthetic hand device 300 includes one or more phalangeal portions 308 interconnected by flexible joint portions 310 to allow flexing or deflection of the digits in prosthetic hand device 300. An additional flexible joint portion 312 can be used to connect the digits to base 302.

In the various embodiments of the invention, the joints referenced herein refers to any type of external or integrally formed joint device or structure that is operable to provide a connection between two portions of a device and that allows movement with one or more degrees of freedom between them. Joint devices and structures can include devices in which movement is provided via a flexible material or moving components. For example, joint devices and structures can include any type of hinge device or structure.

The digits in prosthetic hand device 300 can be actuated using one or more force actuators 314 controlled by a control system 315. As described above, the control system 315 can be configured to monitor the operation of force actuators 314 in accordance with an actuation force and an amount of displacement, as described above with respect to FIG. 2. Additionally, the control system can be coupled to one or more EMG signals to provide one or more actuation input to cause motion of the digits in the prosthetic hand device 300.

The force actuators 314 are connected the distal ends 316 of the digits of prosthetic hand device 300 via one or more actuating structures threaded through the phalangeal portions 308. The actuating structures can include a cable portion 318 and a stack portion 320 located in a phalangeal portion 308 associated with a distal end 316 of each of the digits of prosthetic hand device 300. A description of the stack portion 320 will be provided below with respect to FIG. 4.

In the embodiment shown in FIG. 3, the prosthetic hand device 300 is configured to provide an opposable thumb. In particular, thumb 306 can be connected to base 302 via an opposable portion 322 connected to base 302 with hinge 324. This hinged portion can also be actuated using a force actuator 326 using a actuating structure including a cable portion 328 for apply force to a stack portion 330 in opposing portion.

In operation, the force actuators 314 displace cables 318 (i.e., apply a force to cable 318), causing fingers 304 and thumb 306 to flex according to joints 310. Similarly, force actuator 326 displaces cables 328 (i.e., applies a force to cable 328), causing opposing portion 322 to flex according to hinge 324. Although the digits of prosthetic hand device 300 and opposing portion 322 could potentially flex in any direction, one of ordinary skill in the art would recognize that base 302, phalangeal portions 308, joints 310, opposing portion 322, and hinge 324 can be configured to allow motion in an anterior direction to approximate the motion of digits in a natural hand.

In the embodiment shown in FIG. 3, one or more of the digits of prosthetic hand device 300 can be configured to operate in concert using a single force actuator 314. For example, as shown in FIG. 3, the thumb 306 and index finger 307 are each operated by a separate one of actuators 314 and actuating structures 318. However, the remainder of fingers 304 are configured to operate using actuating structures connected to a single force actuator. Such a configuration can generally be provided in prosthetic hand device 300 since independent motion of a thumb or an index finger is most common in gesturing and grasping or contacting of objects. This configuration also permits a simpler configuration for control system 315, as the control of only 3 fingers and an opposing thumb motion is effectively required. However, the various embodiments of the invention are not limited in this regard and independent control of all digits in hand 300 can be provided.

In some embodiments of the invention, the hand device 300 can be a portion of a larger device, such as a prosthetic arm device. In such embodiments, the hand device 300 can be mechanically coupled to at least one member 332, as shown in FIG. 3. The member 332 can be configured to attachment to a residual limb or other portion of a user's body. The member 332 can include any number of movable joints, including a movable joint at joint 333 between member 332 and hand device 300. For example, as shown in FIG. 3, the member 332 can include a socket 334 for attaching member 332 to a residual limb. However, the various embodiments of the invention are not limited in this regard and member 332 can be configured to be attached to a user's body in any other way. In some embodiments, the member 332 can include sensors 336, such as EMG electrodes. However, the invention is not limited in this regard and the sensors 336 can reside external to the member 332. The configuration of the sensors 336 can be adjusted based on the particular user or source of control signals.

As described above, control of the prosthetic hand device 300 is provided by pre-defining the stiffnesses of the series elastic component and parallel elastic components. In prosthetic hand device 300, the series elastic components are provided by the stack portions 320, 330. A more detailed description of these stack portions will now be provided with respect to FIG. 4.

Figure 4:
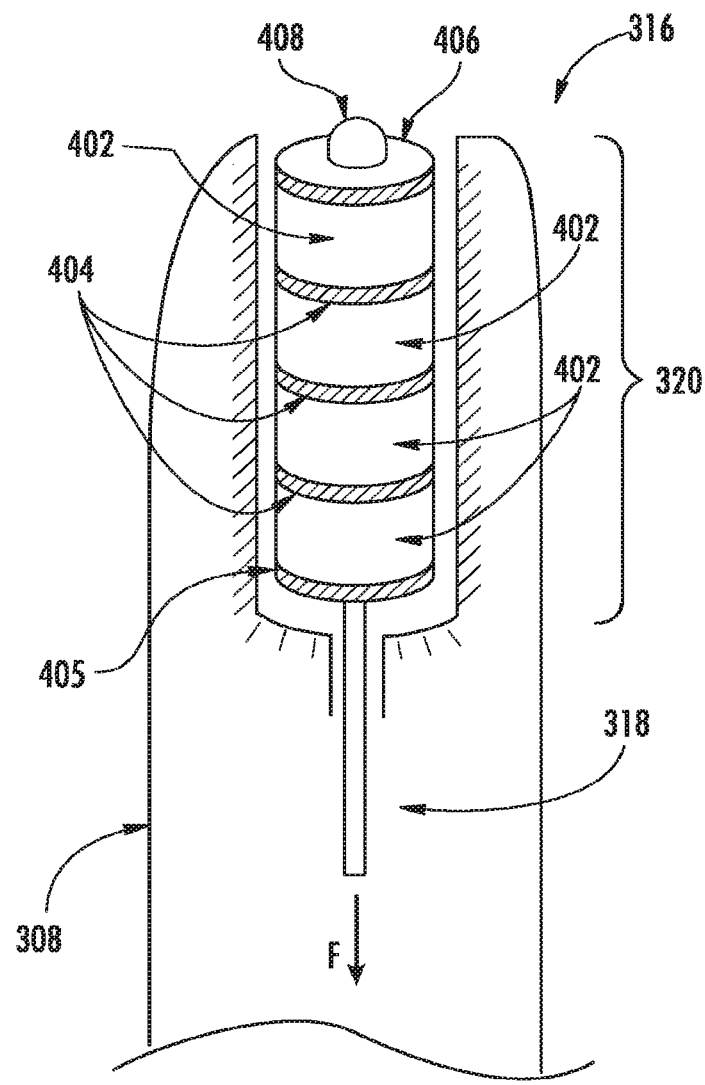
FIG. 4 shows a partial cutaway view of a section of a phalangeal portion associated with a distal end of one of the digits of prosthetic hand device in FIG. 3.

FIG. 4 shows a partial cutaway view of a section of a phalangeal portion 308 associated with a distal end 316 of one of the digits of prosthetic hand device 300. Stack portion 330 is similarly configured, therefore the explanation below is sufficient for describing the operation of stack portion 330.

As shown in FIG. 4, stack portion 320 provides the series elastic component by including an annular layered stack of spring disc devices 402 and thin rigid plates 404, 405, 406, with the cable 318 passing through the center of the discs 402 and plates 404, 405, 406. The cable 318 can include a stopper or head 408 to attach cable 318 to upper plate 406 or sized larger than the annular opening in plate 406 to prevent cable 318 from being disconnected from stack portion 320.

In operation, when a force F is applied to cable 318, the stopper 308 applies force to the plates 404, 405, 406. This force compresses discs 402. As a result of this compression, stack portion 320, and particularly plate 405, exerts force against phalangeal portion 308. The net effect is to provide an series elastic component between phalangeal portion 308 and a force actuator 314. With reference to FIG. 2, the phalangeal portion 308 provides the element 204, the plate 405 provides the connection between the element 204 and the series elastic component 214, the discs 402 provide the series elastic component 214, and the plate 406 provides the connection between the series elastic component 214 and the force actuator 202. In the embodiment in FIG. 4, spring disc devices 402 comprise elastomeric discs operating as compressive spring devices. However, in the various embodiments of the invention, any type of spring device can be used to provide the spring discs, including elastomeric and non-elastomeric spring devices.

Although the discs 402 in FIG. 4 provide a restorative force for the digits in prosthetic hand device 300, thus providing a component of the parallel stiffness, in general this does not provide a parallel stiffness on the order of the series stiffness. As a result, the restorative force provided by the decompression force of the discs 402 may be insufficient to restore prosthetic hand device 300 to a previous or resting position. Accordingly, in some embodiments of the invention, prosthetic hand device 300 can include additional elastic elements to provide the necessary parallel elastic component. An exemplary configuration for prosthetic hand device 300 is shown in FIGS. 5A-5C.

Figures 5A, 5B, 5C:
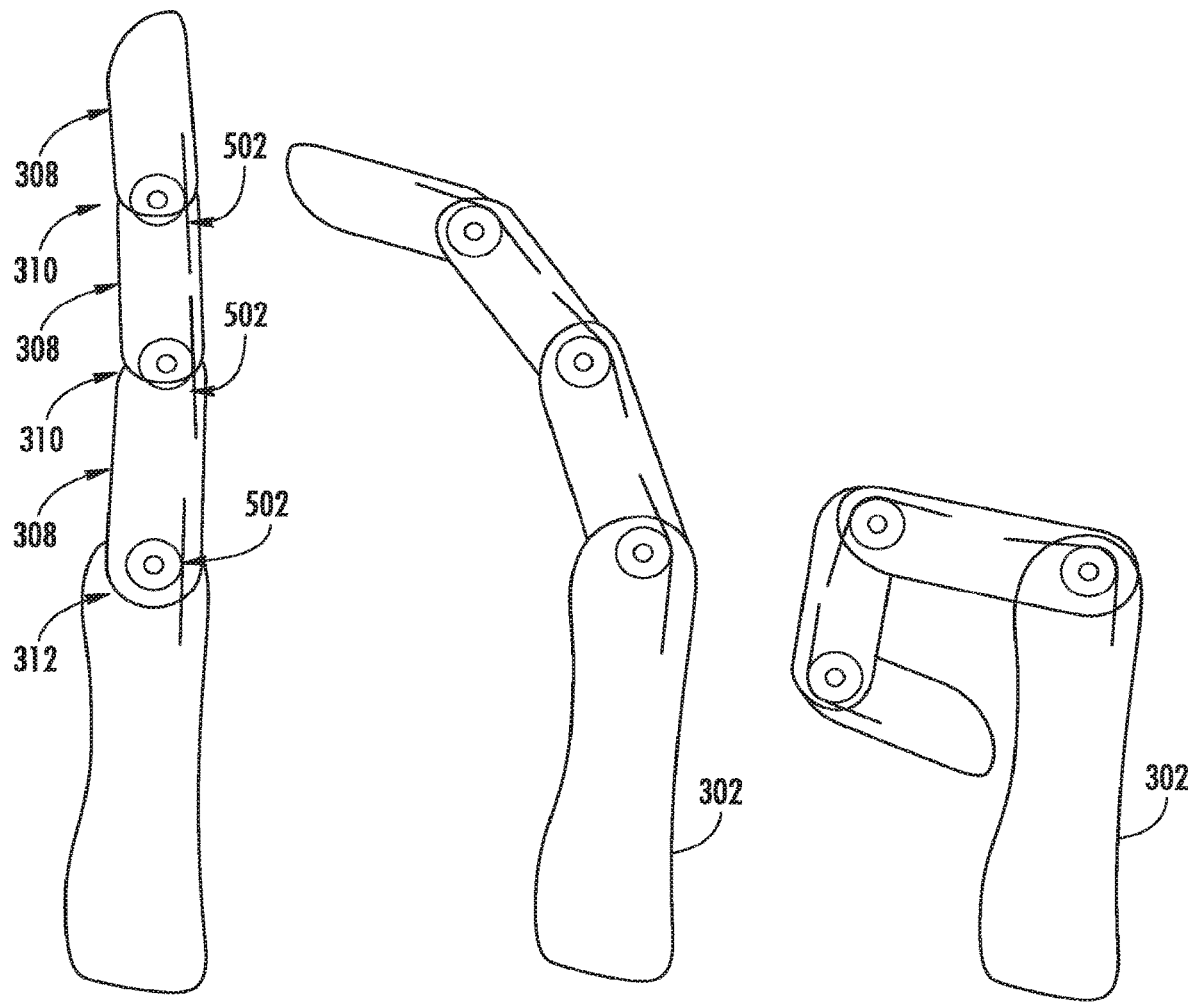
FIGS. 5A-5C show side views of the prosthetic hand device of FIG. 3 in various positions, illustrating one configuration for parallel elastic elements in accordance with an embodiment of the invention.

FIGS. 5A-5C show side views of prosthetic hand device 300 in various positions, where prosthetic hand device 300 is configured to include parallel elastic elements in accordance with an embodiment of the invention. In prosthetic hand device 300, each of joints 310 includes a joint spring device 502 to provide the parallel elastic component. Although FIGS. 5A-5C show spring devices 502 as torsional spring devices, the invention is not limited in this regard. In the various embodiments of the invention, any type of spring device can be used to provide the joint spring devices. In operation, as shown in FIGS. 5B and 5C, the joint spring devices 502 provide increasing restorative force to restore the position of the digits as the digits of prosthetic hand device 300 are flexed or deflected. With respect to FIG. 2, the restorative force of these joint spring devices provide the parallel elastic component 208, as they apply a force to restore a position of element 204 (i.e., the digits of prosthetic hand device 300).

Figure 6:
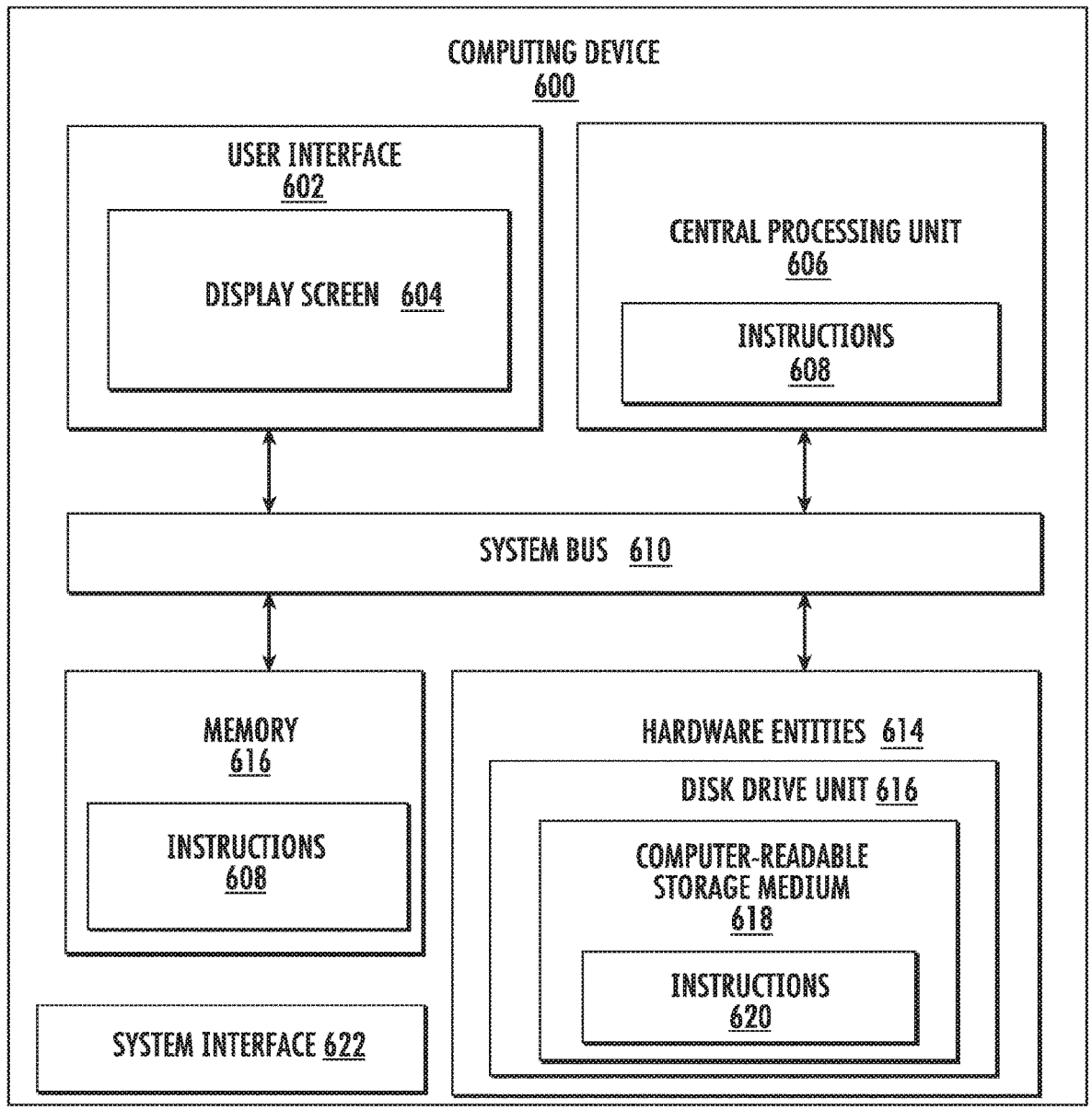
FIG. 6 is block diagram of a computing device which can be implemented as control system in accordance with an embodiment of the invention.

Referring now to FIG. 6, there is provided a detailed block diagram of a computing device 600 which can be implemented as control system 315. Although various components are shown in FIG. 6, the computing device 600 may include more or less components than those shown in FIG. 6. However, the components shown are sufficient to disclose an illustrative embodiment of the invention. The hardware architecture of FIG. 6 represents only one embodiment of a representative computing device for controlling a jointed mechanical device.

As shown in FIG. 6, computing device 600 includes a system interface 622, a Central Processing Unit (CPU) 606, a system bus 610, a memory 612 connected to and accessible by other portions of computing device 600 through system bus 610, and hardware entities 614 connected to system bus 610. At least some of the hardware entities 614 perform actions involving access to and use of memory 612, which may be any type of volatile or non-volatile memory devices. Such memory can include, for example, magnetic, optical, or semiconductor based memory devices. However the various embodiments of the invention are not limited in this regard.

In some embodiments, computing system can include a user interface 602. User interface 610 can be an internal or external component of computing device 600. User interface 602 can include input devices, output devices, and software routines configured to allow a user to interact with and control software applications installed on the computing device 600. Such input and output devices include, but are not limited to, a display screen 604, a speaker (not shown), a keypad (not shown), a directional pad (not shown), a directional knob (not shown), and a microphone (not shown). As such, user interface 602 can facilitate a user-software interaction for launching software development applications and other types of applications installed on the computing device 600.

System interface 622 allows the computing device 600 to communicate directly or indirectly with the other devices, such as an external user interface or other computing devices. Additionally, computing device can include hardware entities 614, such as microprocessors, application specific integrated circuits (ASICs), and other hardware. As shown in FIG. 6, the hardware entities 614 can also include a removable memory unit 616 comprising a computer-readable storage medium 618 on which is stored one or more sets of instructions 620 (e.g., software code) configured to implement one or more of the methodologies, procedures, or functions described herein. The instructions 620 can also reside, completely or at least partially, within the memory 612 and/or within the CPU 606 during execution thereof by the computing device 600. The memory 612 and the CPU 606 also can constitute machine-readable media.

While the computer-readable storage medium 618 is shown in an exemplary embodiment to be a single storage medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure.

The term "computer-readable storage medium" shall accordingly be taken to include, but not be limited to, solid-state memories (such as a memory card or other package that houses one or more read-only (non-volatile) memories, random access memories, or other re-writable (volatile) memories), magneto-optical or optical medium (such as a disk or tape). Accordingly, the disclosure is considered to include any one or more of a computer-readable storage medium or a distribution medium, as listed herein and to include recognized equivalents and successor media, in which the software implementations herein are stored.

System interface 622 can include a network interface unit configured to facilitate communications over a communications network with one or more external devices. Accordingly, a network interface unit can be provided for use with various communication protocols including the IP protocol.

Network interface unit can include, but is not limited to, a transceiver, a transceiving device, and a network interface card (NIC).

Applicants present certain theoretical aspects above that are believed to be accurate that appear to explain observations made regarding embodiments of the invention. However, embodiments of the invention may be practiced without the theoretical aspects presented. Moreover, the theoretical aspects are presented with the understanding that Applicants do not seek to be bound by the theory presented.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A device, comprising:
    at least one deflectable element having a fixed end coupled to a fixed point and a deflectable end;
    at least one actuating structure having a first end coupled to at least said deflectable end of said deflectable element, said actuating structure comprising at least one elastic element in series with at least one non-elastic element;
    at least one force actuator configured to apply an actuator force to a second end of said actuating structure;
        at least one first sensor for detecting a displacement of the deflectable element; and
    a control system for adjusting an operation of said force actuator based on an actuation input signal, an amount of said actuator force, and an amount of the displacement of the deflectable element in response to said amount of said actuator force, wherein the actuation input signal is an input current to an electric motor;
    wherein said non-elastic element comprises at least one cable, wherein said force actuator comprises said electric motor and a pulley for actuating said cable, and wherein said force actuator further comprises a roller clutch between said electric motor and said pulley.

2. The device of claim 1, wherein said control system further comprises a computing device coupled to said at least one sensor, said computing device configured for ascertaining when said deflectable element is in contact with an object and for operating said force actuator using one of a motion control mode and a force control mode based on said ascertaining, said ascertaining comprising detecting when a relationship between said amount of said actuator force and said amount of displacement changes.

3. The device of claim 1, further comprising at least one restorative element coupled to said deflectable element, said restorative element applying a restoring force opposing said actuator force.

4. The device of claim 1, wherein said control system is configured for determining said amount of actuator force based on said input current of said electric motor.

5. The device of claim 1, wherein said control system is configured for determining said amount of displacement based on a position measurement of said electric motor.

6. The device of claim 1, further comprising at least one second sensor for generating said actuation input signal.

7. The device of claim 6, wherein said second sensor comprises an electromyogram sensor.

8. The device of claim 1, wherein said deflectable element comprises a digit of a hand prosthesis.

* * * * *